United States Patent [19]

Dunbar et al.

[11] 4,141,983

[45] Feb. 27, 1979

[54] METHOD FOR INHIBITING ADP-INDUCED PLATELET AGGREGATION USING PHENYLTHIOALKYLAMINES

[75] Inventors: Joseph E. Dunbar; Louis E. Begin; Robert J. Broesma; George D. Dickerson, all of Midland, Mich.

[73] Assignee: The Dow Chemical Company, Midland, Mich.

[21] Appl. No.: 833,124

[22] Filed: Sep. 14, 1977

Related U.S. Application Data

[62] Division of Ser. No. 714,950, Aug. 16, 1976, abandoned.

[51] Int. Cl.$^2$ .......................................... A61K 31/445
[52] U.S. Cl. ................................................... 424/267
[58] Field of Search ......................................... 424/267

[56] References Cited

U.S. PATENT DOCUMENTS 3,988,475  10/1976  Manghisi et al. ................... 424/267

FOREIGN PATENT DOCUMENTS 1,371,650  10/1974  United Kingdom .................... 424/267

Primary Examiner—Frederick E. Waddell
Attorney, Agent, or Firm—James W. Ambrosius

[57]  ABSTRACT

A method for inhibiting blood platelet aggregation in a mammal by administering internally to the mammal an effective amount of a phenylthio(sulfinyl or sulfonyl)alkylamine compound or a pharmaceutically-acceptable salt thereof.

4 Claims, No Drawings

METHOD FOR INHIBITING ADP-INDUCED PLATELET AGGREGATION USING PHENYLTHIOALKYLAMINES

CROSS-REFERENCE TO RELATED APPLICATION

This is a division, of application Ser. No. 714,950 filed Aug. 16, 1976 now abandoned.

BACKGROUND OF THE INVENTION

Adenosine diphosphate, hereafter called ADP, is a principle factor in the aggregation of blood platelets. Platelet aggregation in the blood vessel of a mammal can lead to the formation of a thrombus. Agents which interfere with ADP-induced platelet aggregation are of use as antithrombotic drugs.

Substituted phenyl (N,N-dialkylamino)alkyl sulfides have been described in British Pat. No. 718,322. Other phenyl alkyl sulfides having dialkylamino or arylamino groups attached to the alkyl are also known from the literature. See Chawla et al., *J. Med. Chem.* 13, 480 (1970); Schuetz et al., *J. Amer. Chem. Soc.* 80, 162 (1958); Kim et al., *J. Amer. Chem. Soc.* 74, 5102 (1952); Chem. Abstracts 79:18712; and British Pat. No. 1,371,650. Known phenyl alkylsulfides have displayed pharmacological properties as analgesics, anesthetics, central muscle relaxants, diuretics, and bactericides. In addition, analogs of N-(2-(4-chlorophenylthio)ethyl)-N,N-diethylamine hydrochloride have been studied as inhibitors of carotenoid biosynthesis in *Phycomyces blakesleeanus.* See Elahi, *Phytochemistry* 14, 133 (1975). Aminoalkyl aryl sulfides have been described by Karaulova et al. in *Khimiia Geterotsiklicheskilah Soedinenii* 11, No. 6, 759–764 (1975). None of the known compounds have been reported to have an inhibitory effect on the aggregation of blood platelets.

Various (aminoalkylthio)heterocyclic compounds are shown in the literature to be platelet aggregation inhibitors. See Elslager et al., *J. Med. Chem.* 15(1), 61 (1972) and Elslager et al., *J. Heterocyclic Chem.* 9, 1109 (1972).

SUMMARY OF THE INVENTION

The present invention relates to a method for inhibiting the aggregation of blood platelets in a mammal using compounds of the general formula:

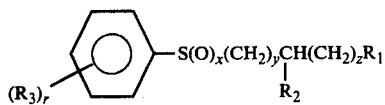

wherein:
- $R_1$ is a diloweralkylamino group such as for example, dimethylamino, diethylamino, dipropylamino, diisopropylamino, or dibutylamino, a dicycloalkylamino group such as for example, dicyclohexylamino, or a cycloimino group such as for example, piperidino, hexamethyleneimino, or morpholino;
- $R_2$ is a lower alkyl, morpholino, 4-morpholinylmethyl, or hydrogen;
- $R_3$ is lower alkyl, halo, hydroxy, amino, acetamido, acetoxy, lower alkoxy, or carboxy;
- $r$ is an integer of from 0 to 5;
- $x$ is an integer of from 0 to 2;
- $y$ is an integer of from 0 to 4 with the proviso that when $R_2$ is lower alkyl or morpholino, $y$ is 1 and when $R_2$ is 4-morpholinylmethyl $y$ is 0; and
- $z$ is an integer of from 0 to 3 with the proviso that when $R_2$ is hydrogen $z$ is 0.

It is further understood that when $r$ is greater than 1, $R_3$ may represent either a multiple of the same group or a combination of any of the groups described above attached to the phenyl ring.

As used in the specification and claims, the term lower alkyl or lower alkoxy refers to an alkyl or alkoxy having from 1 to about 5 carbon atoms.

The invention also includes the pharmaceutically-acceptable salts of the substituted phenylthioalkylamine compounds described herein. As used in the specification and claims, the term "pharmaceutically-acceptable salts" refers to non-toxic acid addition salts of the substituted phenylthioalkylamine compounds, the anions of which are relatively innocuous to animals at dosages consistent with good platelet aggregation inhibition so that the beneficial effects of the free base are not vitiated by the side effects ascribable to the anions. Pharmaceutically-acceptable salts include those derived from mineral acids such as hydrochloric and sulfuric acids and from organic acids such as lactic, maleic, succinic, fumaric, glutaric, citric, malic, p-toluenesulfonic, methanesulfonic and tartaric acids, and the like.

In general, the compounds of the present invention may be administered in daily dosages of from about 1.8 mg to about 400 mg of active ingredient per kilogram of body weight as platelet aggregation inhibiting agents. The compounds are administered internally to a mammal either orally or parenterally by subcutaneous, intravenous or intraperitoneal injection or the like, or by implantation or the like, oral administration being preferred. The blood platelet aggregation inhibiting amount of the compounds of the invention to be administered internally to a mammal, that is the amount which is effective to substantially inhibit the aggregation of blood platelets in the presence of ADP, can vary depending upon such factors as the animal treated, the particular compound administered, the period of administration, and the method of administration.

DETAILED DESCRIPTION OF THE INVENTION

Compounds used in the present invention may be prepared by reacting a corresponding substituted benzenethiol with a dialkylaminoalkyl halide, dicycloalkylaminoalkyl halide or cycloiminoalkyl halide. The reaction is usually carried out under alkaline conditions. In general, the reaction may be represented by the general formula:

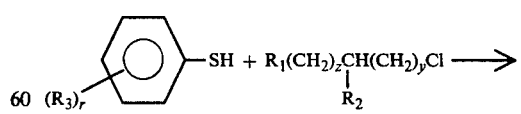

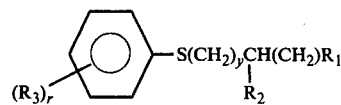

wherein $r$, $x$, $y$, $z$, $R_1$, $R_2$, and $R_3$ represent the same integer and groups as described above.

Sulfinyl and sulfonyl derivatives of the sulfides prepared above may be obtained by oxidizing the sulfur with an oxidizing agent such as hydrogen peroxide. Sulfonyl derivatives have also been prepared directly by reacting substituted benzenesulfinic acid or a sulfinate salt thereof with the aminoalkyl halide.

As noted above, compounds used in the practice of the present invention are potent inhibitors of ADP-induced platelet aggregation and are effective antithrombotic agents. It was also found that structural changes in the compounds produced changes in potency and effectiveness. In general, substitution on the phenyl ring was found to increase the potency of the compounds as platelet aggregation inhibitors. Multiple substitution on the phenyl ring also produced dramatic increases in potency in some cases. It was found that the most desirable substitutions on the phenyl ring were hydroxy, lower alkyl, and lower alkoxy with hydroxy and alkyl being particularly preferred.

The oxidation level of the sulfur also was found to effect the antithrombotic activity of the compounds. In general, compounds having a sulfide, that is where $x$ is 0, showed the best activity in vitro. However, in vivo studies indicate that those compounds having a sulfonyl group are more effective as antithrombotic agents in mammals. Thus, methods using the sulfonyl derivatives are particularly preferred for inhibiting platelet aggregation.

Branching of the carbon chain by a lower alkyl or morpholino group between the phenyl and amino moieties in some instances also produced a marked improvement in the activity of the compound.

Compounds used in the practice of the invention having as their amine moieties dimethylamino, diethylamino, dicyclohexylamino or piperidino, while still operable as antithrombotics, were found in some cases to have cardiovascular side effects which narrowed the margin of safety between the dose levels required to achieve the desired antithrombotic activity and the toxic levels at which undesirable side effects occurred in the animals. For this reason, compounds having a morpholino group are preferred. It was found that compounds having the morpholino group attached to the alkyl portion gave good inhibition of ADP-induced platelet aggregation and could be administered at relatively high dosages without showing any significant toxic effects on the treated animal.

Examples 1 through 7 serve to illustrate the preparation of representative member compounds used in the practice of the present invention but are not to be construed as a limitation thereon.

EXAMPLE 1

Preparation of
4-(3-(4-Hydroxyphenylthio)propyl)morpholine

A mixture was prepared containing 55.5 grams (0.440 mole) of 4-hydroxybenzenethiol, 88.0 grams (0.440 mole) of 20% sodium hydroxide, and 160 ml of water. To this 72.0 grams of 4-(3-chloropropyl)morpholine was added. The reaction mass was heated to reflux with stirring and immediately cooled and diluted with water. The product separated out as an oil, but crystallized upon standing. Recrystallization from methylcyclohexane and ethanol gave white crystals of 4-(3-(4-hydroxyphenylthio)propyl)morpholine having a melting point of 130.5°–131° C.

Elemental analysis showed carbon 61.9%, hydrogen 7.43%, and nitrogen 5.45% as compared to theoretical percentages of 61.62, 7.56, and 5.53 respectively.

EXAMPLE 2

4-(3-(4-Hydroxyphenylsulfinyl)propyl)morpholine
p-Toluenesulfonic Acid Salt

A mixture was prepared containing 48.5 grams (0.114 mole) of 4-(3-(4-hydroxyphenylthio)propyl)morpholine toluenesulfonic acid salt and 200 ml of glacial acetic acid. To this stirred mixture 12.5 grams (0.110 mole) of 30% hydrogen peroxide was added at such a rate as to keep the temperature of the reaction mixture below 30° C. The resulting solution was stirred at room temperature for three hours after which period of time the solvent was removed by evaporation under reduced pressure. The residue was dissolved in water, and the pH was adjusted to 7.3 by the addition of dilute sodium hydroxide solution. The mixture was extracted with methylene chloride, the extract dried over anhydrous magnesium sulfate and the solvent removed by evaporation in vacuo. The crude free base was obtained as an oil. The oil was dissolved in propanol-2, and the solution was treated with p-toluenesulfonic acid in a propanol-2 solution. The crude 4-(3-(4-hydroxyphenylsulfinyl)-propyl)morpholine p-toluenesulfonic acid salt precipitated and was recrystallized from nitromethane to give a white, crystalline solid having a melting point of 167°–168° C.

Elemental analysis showed carbon 54.7%, hydrogen 6.24%, and nitrogen 3.21% as compared to theoretical amounts of carbon 54.40%, hydrogen 6.16%, and nitrogen 3.17%.

EXAMPLE 3

4-(3-(4-Hydroxyphenylsulfonyl)propyl)morpholine
Hydrochloride

A first solution of 19.0 grams (0.0999 mole) of p-toluenesulfonic acid monohydrate in propanol-2 was added with stirring to a second solution containing 25.0 grams (0.0987 mole) of 4-(3-(4-hydroxyphenylthio)-propyl)morpholine and 400 ml of warm propanol-2. The p-toluenesulfonic acid salt precipitated and was suspended in 200 ml of glacial acetic acid. Thirty percent hydrogen peroxide (23.0 grams, 0.203 mole) was added slowly to the stirred suspension while keeping the temperature of the reaction mixture below 35° C. by means of a cooling bath. After the addition was complete the mixture was kept at 55° to 60° C. for a period of 15 hours. Excess hydrogen peroxide was destroyed by warming the reaction mixture to 95° C. The acetic acid was removed by evaporation in vacuo. The residue was dissolved in water, and the pH of the solution adjusted to the isoelectric point (about 8.0). The mixture was extracted with methylene chloride and the extract dried over anhydrous sodium sulfate. The solvent was removed by evaporation in vacuo, and the residue was dissolved in ethanol. The solution was treated with an excess of ethanolic hydrogen chloride to give 14.0 grams of 4-(3(4-hydroxyphenylsulfonyl)propyl)morpholine hydrochloride as a white crystalline solid. Following vacuum drying the melting point was found to be 197°–198° C.

Elemental analysis showed carbon 48.7%, hydrogen 6.18%, and nitrogen 4.58% as compared to theoretical values of carbon 48.51%, hydrogen, 6.26%, and nitrogen 4.35%.

EXAMPLE 4

4-(2-(4-Acetamidophenylsulfonyl)ethyl)morpholine

Sodium carbonate (11.0 grams, 0.104 mole) was added to a stirred mixture of 9.96 grams (0.0500 mole) of 4-acetamidobenzenesulfinic acid, 9.30 grams (0.0500 mole) of 2-(4-morpholino)ethylchloride hydrochloride, and 100 ml of water. The reaction mixture was warmed for 1¼ hours at 65° C. At the end of this period of time, the mixture was cooled, extracted with methylene chloride, and the extract dried over anhydrous magnesium sulfate. The solvent was removed by evaporation in vacuo, and the residue was crystallized from ethanol to give white crystals of 4-(2-(4-acetamidophenylsulfonyl)ethyl)morpholine having a melting point of 136°–137° C.

Elemental analysis showed carbon 53.89%, hydrogen 6.35%, and nitrogen 8.89% as compared to theoretical values of carbon 53.82%, hydrogen 6.45%, and nitrogen 8.97%.

EXAMPLE 5

4-(4-(4-Hydroxyphenylthio)butyl)morpholine

A mixture of 26.4 g (0.209 mole) of p-mercaptophenol, 40.0 g (0.209 mole) of 4-(4-chlorobutyryl)morpholine, 42 ml (0.21 mole) of 5N sodium hydroxide and 400 ml of water was heated to boiling and cooled, causing the precipitation of the solid intermediate product, 4-(4-(4-hydroxyphenylthio)butyryl)morpholine. The crude intermediate was dried and recrystallized from benzene as white crystals having a melting point of 123°–124° C.

Elemental analysis showed carbon 59.6%, hydrogen 6.94% and nitrogen 4.95% as compared to theoretical values of 59.78%, 6.81%, and 4.98%, respectively.

To a stirred suspension of 4.2 g (0.11 mole) of lithium aluminum hydride in 200 ml of tetrahydrofuran was added in small portions and with ice bath cooling 15 g (0.053 mole) of 4-[4-(4-hydroxyphenylthio)butyryl]morpholine. After the addition was complete the reaction mixture was heated under reflux with stirring for 1 hour and cooled. Four ml of water was added, followed by 4 ml of 20% sodium hydroxide and then 12 ml more water. The inorganic salts, thus precipitated, were removed by filtration, and the filtrate was acidified with concentrated hydrochloric acid and then made slightly basic by the addition of concentrated ammonium hydroxide, causing the precipitation of the crude 4-(4-4-hydroxyphenylthio)butyl)morpholine as a pink gum that solidified on standing. The crude product was recrystallized from aqueous ethanol. The white crystals had a melting point of 95°–97° C.

Elemental analysis showed carbon 62.8%, hydrogen 7.92%, and nitrogen 5.41% as compared to theoretical values of 62.90%, 7.92% and 5.24%.

EXAMPLE 6

4-(5-(4-Hydroxyphenylthio)pentyl)morpholine

A mixture of 47.9 g (0.250 mole) of p-mercaptophenol, 51.4 g (0.250 mole) of 4-(5-chlorovaleryl)morpholine, 52 ml of 5N sodium hydroxide and 600 ml of water was heated to boiling and then stirred at 50°C. for 1 hour; and, thereafter, stirred at room temperature for 15 hours. The white, crystalline intermediate precipitated during this period. The dried, crude intermediate was recrystallized from benzene to give the intermediate, 4-[5-(4-hydroxyphenylthio)valeryl]morpholine, as white crystals, mp 112°–113° C.

Elemental analysis showed carbon 61.09%, hydrogen 7.13% and nitrogen 4.90% as compared to theoretical values of 61.00%, 7.17% and 4.74%.

Lithium aluminum hydride reduction of the amide was accomplished according to the procedure of Example 5, giving 26.1 g of the 4-(5-(4-hydroxyphenylthio)pentyl)morpholine as a white solid. Recrystallization from ethanol gave the product as white crystals, mp 168°–171° C.

Elemental analysis showed carbon 63.2%, hydrogen 8.12% and nitrogen 5.12% as compared to theoretical values of 64.02%, 8.24% and 4.98%.

EXAMPLE 7

2-(2-(Diisopropylamino)ethylthio)-1,4-hydroquinone Hydrochloride

To a stirred solution of 19.8 g (0.100 mole) os 2-(diisopropylamino)ethanethiol hydrochloride in 150 ml of acetonitrile heated under reflux a solution containing 10.8 g (0.100 mole) of p-benzoquinone in 75 ml of acetonitrile was added dropwise over a period of 1 hour and 20 minutes. After the addition was complete, the reaction mixture was refluxed an additional 10 minutes and then cooled with stirring by means of an ice bath. The resulting grey, crystalline solid was collected on a filter, washed with ethylacetate and dried in vacuo over calcium chloride. One recrystallization from methanol and one from ethanol gave the 2-(2-(diisopropylamino)ethylthio)-1,4-hydroquinone hydrochloride as white crystals, mp 159.5°–160° C.

Elemental analysis showed carbon 55.3%, hydrogen 7.83%, nitrogen 4.75% was compared to theoretical values of 54.97%, 7.91% and 4.58%, respectively.

In addition to the compounds described above in Examples 1 through 7, a number of other compounds were prepared which may be used in the practice of the present invention. The compounds are as follows:

4-(2-(4-hydroxyphenylthio)ethyl)morpholine, m.p. 115°–116° C.

4-(2-(4-hydroxyphenylsulfinyl)ethyl)morpholine, m.p. 143.5°–114.5° C.

4-(2-(4-hydroxyphenylsulfonyl)ethyl)morpholine, m.p. 152°–153° C.

4-(2-(4-acetoxyphenylsulfonyl)ethyl)morpholine, m.p. 117°–117.5° C.

4-(3-(4-acetamidophenylsulfonyl)propyl)morpholine, m.p. 113.5°–115° C.

N-(3-(4-hydroxyphenylthio)propyl)dimethylamine, m.p. 80°–81° C.

N-(3-(4-hydroxyphenylsulfonyl)propyl)dimethylamine m.p. 165°–166° C.

1-(2-(4-hydroxyphenylthio)ethyl)hexamethyleneimine, m.p. 110°–110.5° C.

4-(2-(2-carboxyphenylthio)ethyl)morpholine hydrochloride, m.p. 213°–214° C.

4-(3-(4-hydroxyphenylthio)-2-methylpropyl)morpholine p-toluenesulfonic acid salt, m.p. 132°–133° C.

4-(3-(4-hydroxyphenylsulfonyl)-2-methylpropyl)morpholine hydrochloride, m.p. 253°–254° C.

4-((2,3-di-4-morpholinylpropyl)thio)phenol methanesulfonate, m.p. about 178° C.

N-(3-(4-hydroxyphenylthio)propyl)diisopropylamine hydrochloride, m.p. 155°–156.5° C.

N-(3-(4-hydroxyphenylthio)propyl)dicyclohexylamine hydrochloride, m.p. 174°–176° C.
N-(3-(4-hydroxyphenylthio)propyl)piperidine, m.p. 121.5°–122.5° C.
N-(3-(4-hydroxyphenylsulfonyl)propyl)dicyclohexylamine hydrochloride isopropylate, m.p. 133°–135° C.
N-(3-(4-hydroxyphenylsulfonyl)propyl)diisopropylamine hydrochloride, m.p. 175°–177° C.
N-(3-(4-hydroxyphenylsulfinyl)propyl)diisopropylamine hydrochloride, m.p. 154°–156° C.
4-(3-(4-hydroxyphenylsulfonyl)propyl)morpholine, m.p. 121°–122° C.
4-(3-(4-hydroxyphenylsulfonyl)propyl)morpholine, p-toluenesulfonate, m.p. 155.5°–156.5° C.
4-(3-(4-hydroxyphenylsulfonyl)propyl)morpholine succinate, m.p. 156.5°–157.5° C.
N-(3-(4-hydroxyphenylsulfinyl)propyl)piperidine p-toluenesulfonate, m.p. 170°–171° C.
4-(3-(4-hydroxyphenylthio)propyl)morpholine hydrochloride, m.p. 130°–131° C.
4-(3-(4-hydroxyphenylthio)propyl)morpholine p-toluenesulfonate, m.p. 126.5°–127° C.
N-(3-(4-hydroxyphenylsulfonyl)propyl)piperidine p-toluenesulfonate, m.p. 141°–141.5° C.
2-(diethylamino)ethyl phenyl sulfide hydrochloride, m.p. 101°–101.5° C.
2-(4-morpholinyl)ethyl p-tolyl sulfide hydrochloride, m.p. 170°–171° C.
3-(dimethylamino)propyl phenyl sulfide p-toluenesulfonic acid salt, m.p. 109°–109.5° C.
4-fluorophenyl 2-(4-morpholinyl)ethyl sulfide p-toluenesulfonic acid salt, m.p. 131.5°–132.5° C.
2-(4-morpholinyl)ethyl pentafluorophenyl sulfide p-toluenesulfonic acid salt, m.p. 185°–186° C.
4-(2-(phenylsulfinyl)ethyl)morpholine hydrochloride, m.p. 188°–189° C.
4-(2-(phenylsulfonyl)ethyl)morpholine hydrochloride, m.p. 231°–232° C.
4-(2-(4-fluorophenylsulfonyl)ethyl)morpholine p-toluenesulfonic acid salt, m.p. 221°–222° C.
4-(2-(p-tolylsulfonyl)ethyl)morpholine p-toluenesulfonic acid salt, m.p. 210°–211° C.
2-(2-diisopropylamino)ethylthio)-1,4-hydroquinone hydrochloride, m.p. 159.5°–160° C.
2-(2-(diethylamino)ethylthio)-3,6-dimethyl-1,4-hydroquinone hydrochloride, m.p. 143°–144.5° C.
4-(3-(4-methoxyphenylsulfonyl)propyl)morpholine p-toluenesulfonic acid salt, m.p. 176.5°–178° C.
4-(3-(phenylsulfonyl)propyl)morpholine, m.p. 62°–65° C.
4-(3-(2-aminophenylthio)propyl)morpholine, m.p. 63.5°–64.5° C.
2-(1-piperidyl)ethyl phenyl sulfide hydrochloride, m.p. 190°–191° C.
4-(5-(p-tolylsulfonyl)pentyl)morpholine methanesulfonic acid salt, m.p. 109.5°–110.5° C.
4-(2-(4-chlorophenylsulfonyl)ethyl)morpholine methanesulfonic acid salt, m.p. 188°–189° C.
4-(2-(phenylthio)ethyl)morpholine hydrochloride, m.p. 130°–131° C.
N-(2-(phenylthio)ethyl)diethylamine hydrochloride, m.p. 101°–101.5° C.
4-(3-(p-tolylsulfonyl)propyl)morpholine hemisuccinic acid salt, m.p. 88°–89° C.
4-(2-(3,4-dichlorophenylthio)ethyl)morpholine hydrochloride, m.p. 187.5°–188° C.
4-(2-(4-methoxyphenylsulfonyl)ethyl)morpholine methanesulfonic acid salt, m.p. 177°–178° C.
4-(2-(2,3,4,5,6-pentafluorophenylsulfinyl)ethyl)morpholine p-toluenesulfonic acid salt, m.p. 133°–134° C.
4,4'-((1-(phenylthio)methyl)-1,2-ethanediyl)-bis-morpholine methanesulfonate (1:2), m.p. 196°–197° C.
4,4'-(1-(((4-methylphenyl)sulfonyl)methyl)-1,2-ethanediyl)-bis-morpholine methanesulfonate (1:2), m.p. 198°–199° C.
4,4'-(1-(((4-methylphenyl)thio)-1,2-ethanediyl)-bis-morpholine methanesulfonate (1:2), m.p. 239.5°–240° C.
4,4'-(1-(((4-methoxyphenyl)thio)methyl)-1,2-ethanediyl)-bis-morpholine methanesulfonate (1:2), m.p. 211.5°–212.5° C.
4,4'-(1-(((4-methoxyphenyl)sulfonyl)methyl)-1,2-ethanediyl)-bis-morpholine methanesulfonate (1:2), m.p. 186.5°–187.5° C.
4-(3-(4-aminophenylthio)propyl)morpholine p-toluenesulfonic acid salt, m.p. 167°–167.5° C.
4-(3-(4-bromophenylthio)propyl)piperidine hydrochloride, m.p. 166.5°–167.5° C.
4-(3-(4-bromophenylthio)propyl)morpholine methanesulfonic acid salt, m.p. 114.5°–115° C.
4-(3-(4-bromophenylsulfonyl)propyl)morpholine, m.p. 94°–95° C.
4,4'-(2-(phenylthio)-1,3-propanediyl)-bis-morpholine methanesulfonate (1:2), m.p. 195°–196° C.
4,4'-(2-(phenylsulfonyl)-1,3-propanediyl)-bis-morpholine methanesulfonate (1:2), m.p. 162.5°–164° C.
4,4'-(2-((4-methoxyphenyl)sulfonyl)-1,3-propanediyl)-bis-morpholine methanesulfonate (1:2), m.p. 187°–188° C.

The following examples illustrate the use of the above described compounds in the practice of the present invention, however, these examples are not to be construed as a limitation upon the present invention.

EXAMPLE 8

In vitro Inhibition of ADP-induced Platelet Aggregation

Platelet aggregation was demonstrated by techniques originally described by Born in *Nature* 194, 927 (1962). Using this technique, platelet aggregation was initiated in platelet rich plasma by 0.0625–1.0 µg/ml of ADP. Rat blood was collected into a 3.0% sodium citrate solution by cardiac puncture under methoxyfurane anesthesia. The blood was centrifuged at 120X g for about 10 minutes at room temperature and the supernatant platelet rich plasma was removed and diluted with lactated Ringer's solution containing the inhibitory agent. Samples of 1.0 ml were pipetted into plastic-test tubes and incubated at 37° C. for 10 minutes. Platelet aggregation in response to the ADP challenge was measured on a Chrono-Log Aggregometer at 37° C. The concentration that produced 50% of the maximum response for each agent ($IC_{50}$) was established by determining a concentration-response relationship by linear regression analysis.

Using the in vitro technique outlined above, the compound 4-(3-(4-hydroxyphenylsulfonyl)propyl)morpholine hydrochloride showed an $IC_{50}$ of 8.8 µM/ml of ADP. In general, the compounds used in the practice of the present invention showed $IC_{50}$ values ranging from about 0.6 to 10 µM/ml for ADP.

EXAMPLE 9

In vivo Inhibition of ADP-induced Platelet Aggregation

Measurement of platelet aggregation in vivo was carried out using the technique described by Broersma, et al., *Thomb. diath. Haemorrhag.* 29, 201 (1973). Such determinations are based upon the measurement of the blood pressure proximal to a filter with 53 micron openings through which arterial blood flows. Platelet aggregation partially obstructs the filter with time causing a change in the pressure which is proportional to the degree of platelet aggregation (thrombosis).

Fasted male beagle dogs were anesthetized with sodium pentobarbital (35 mg/kg), heparinized (16.5 μ/kg, i.v.) and tested for platelet function using aggregometry. Compounds were administered intravenously in solutions having the pH adjusted to 7.4. The solution was infused at a rate of 15.3 ml/min to total volume of 5 ml/kg of body weight. Thrombus formation was observed using the filter occlusion technique outlined above. Platelet count, hematocrit, blood pressure, and heart rate were also measured. The compound 4-(3-(Hydroxyphenylsulfonyl)-propyl)morpholine hydrochloride was found to be particularly active in inhibiting platelet aggregation. The antithrombotic activity of this compound was found to be significantly different from aspirin, a recognized antithrombotic agent (see Evans, et al., *J. Exp. Med.* 128, 877), in that it inhibits the rate of both ADP and collagen-induced platelet aggregation after intravenous administration to dogs in doses as low as 5.6 μmoles/kg of body weight.

The compound (4-(3-hydroxyphenylsulfonyl)-propyl)-morpholine hydrochloride was also administered orally to dogs. Measurement of platelet aggregation using filter occlusion indicated there was no significant difference in activity between infusion and oral administration. The compound was also administered orally and by infusion to monkeys (*Macaca mulatta*) and platelet aggregation measured using the method described hereinabove. Dosages of 56 μmoles/kg (i.v.) were used and found to give satisfactory platelet aggregation inhibition in monkeys.

We claim:

1. A method for inhibiting ADP-induced platelet aggregation and treating thrombosis in a mammal in need thereof comprising administering internally to said mammal a platelet aggregation inhibiting amount of a compound corresponding to the formula:

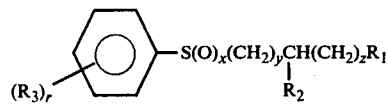

and the pharmaceutically-acceptable salts thereof wherein:
- $R_1$ is piperidino;
- $R_2$ is lower alkyl or hydrogen;
- $R_3$ is, lower alkyl, halo, hydroxy, amino, acetamino, acetoxy, lower alkoxy, or carboxy;
- $r$ is an integer of from 0 to 5;
- $x$ is an integer of from 0 to 2;
- $y$ is an integer of from 0 to 4 with the proviso that when $R_2$ is lower alkyl, $y$ is 1; and
- $z$ is an integer of from 0 to 3 with the proviso that when $R_2$ is hydrogen $z$ is 0.

2. The method of claim 1 wherein $R_3$ of the compound is lower alkyl, lower alkoxy, and hydroxy.

3. The method of claim 1 wherein $x$ is 2.

4. The method of claim 1 wherein the compound is 2-(1-piperidinyl)ethyl phenyl sulfide and the pharmaceutically-acceptable salts thereof.